(12) United States Patent
Kim

(10) Patent No.: US 9,329,145 B2
(45) Date of Patent: May 3, 2016

(54) MATERIAL SCREENING APPARATUS

(75) Inventor: Keehoon Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 464 days.

(21) Appl. No.: 13/812,290

(22) PCT Filed: Jul. 27, 2010

(86) PCT No.: PCT/KR2010/004917
§ 371 (c)(1),
(2), (4) Date: Feb. 27, 2013

(87) PCT Pub. No.: WO2012/015077
PCT Pub. Date: Feb. 2, 2012

(65) Prior Publication Data
US 2013/0156063 A1    Jun. 20, 2013

(51) Int. Cl.
*G01K 7/00* (2006.01)
*G01N 25/20* (2006.01)
*G01N 25/18* (2006.01)

(52) U.S. Cl.
CPC ............... *G01N 25/20* (2013.01); *G01N 25/18* (2013.01)

(58) Field of Classification Search
USPC ...................................... 374/44, 43
See application file for complete search history.

(56) References Cited

U.S. PATENT DOCUMENTS

| 7,658,119 B2 | 2/2010 | Loeb et al. |
| 2005/0058178 A1 | 3/2005 | Shih et al. |

FOREIGN PATENT DOCUMENTS

| JP | 55-132939 A | 10/1980 |
| JP | 09-192473 A | 7/1997 |
| JP | 2008-051744 A | 3/2008 |
| KR | 20-0380052 Y1 | 3/2005 |

OTHER PUBLICATIONS

Translation JP 2008-051744 (Mar. 6, 2008).*
International Search Report mailed Apr. 29, 2011, issued in counterpart International Patent Application No. PCT/KR2010/004917; 5 pages including English translation.

* cited by examiner

*Primary Examiner* — Mirellys Jagan
(74) *Attorney, Agent, or Firm* — NSIP Law

(57) ABSTRACT

The present invention relates to a material screening apparatus, and more particularly, to a material screening apparatus that senses temperature change according to the thermal characteristics of the material to be screened so as to extract a thermal characteristic value for the material and determine the type of the material. The material screening apparatus according to an embodiment of the present invention comprises: a plurality of heat generators for variably generating heat; a plurality of temperature sensors attached to the heat generators, respectively, for measuring the changing temperatures of the heat generators; and a controller for controlling the heat generation by the heat generators, performing the calculations of the temperature values measured by the plurality of temperature sensors, and outputting the thermal characteristic value of the material.

4 Claims, 2 Drawing Sheets

MATERIAL SCREENING APPARATUS

Cross-Reference to Related Applications

This application is a National Stage of International Application No. PCT/KR2010/004917, filed Jul. 27, 2010 and published as WO2012/015077 A1 on Feb. 2, 2012, the entire disclosures of which are incorporated herein by reference for all purposes.

TECHNICAL FIELD

The present disclosure relates to a material screening apparatus, and more particularly, to a material screening apparatus, which determines the kind of a material by sensing a temperature change according to a thermal conductivity characteristic of the material to be identified and then extracting a thermal feature value of the material.

BACKGROUND ART

In daily life and at industrial sites, it is sometimes required to check a material of a specific article. In other words, in the manufacturing or construction fields, kinds of supplied materials should be checked prior to launching a work. In addition, in the daily life, according to circumstances, the kind of a material should be checked in order to prevent a contact with a dangerous material.

Recently, a robot prosthetic hand is being actively studied, and the tactile impression is an important element when manipulating an article by using a prosthetic hand. For this, it is important to attach a tactile sensor to the prosthetic hand in order to feel the tactile impression. In particular, temperature transmission is important in a social aspect where humans and other animals feel sensations as well as in a functional aspect where an article is manipulated. In addition, temperature transmission plays an important role when determining the material of a touched article. Therefore, there is needed a device which is attached to a robot prosthetic hand to precisely determine temperature and material of an article.

Meanwhile, in case of a surgical robot or a cell manipulation robot, force sensor or vision information is used to sense a manipulated article, which however requires a large-sized system. Therefore, it is needed to develop a device capable of searching various materials and identifying an article of a desired material.

DISCLOSURE OF INVENTION

Technical Problem

The present disclosure is directed to providing a material screening apparatus, which may rapidly and accurately calculate a thermal feature value of a material with a simple structure.

The present disclosure is also directed to providing a material screening apparatus, which may easily check a thermal feature value of a material by simply contacting the material to be identified.

Technical Solution

In one aspect, there is provided a material screening apparatus, which identifies a material by contacting a surface of the material and calculating a thermal feature value of the material, the apparatus including: a plurality of heat generators for individually generating heat; a plurality of temperature sensors respectively attached to the heat generators to measure varying temperatures of the heat generators; and a controller for controlling heat generation of the heat generators, processing temperature values measured by the plurality of temperature sensors, and calculating a thermal feature value of the material.

The controller may include a storage unit where inherent thermal feature values of a plurality of materials are stored in advance; and a comparing unit for comparing the thermal feature value of the material, calculated from the temperature values measured by the plurality of temperature sensors, with data values stored in the storage unit to find a coincident value.

The controller may further include a display unit for displaying an identification result of the material, checked by the comparing unit.

The material screening apparatus may further include a pressure sensor for, when the heat generator contacts the material to be identified, sensing a pressure change caused by the contact and intercepting heat generation of the heat generators.

The controller may calculate thermal effusivity, which is the thermal feature value of the material, by applying the temperature values measured by the temperature sensors to Equation 7 below:

$$\beta_{obj} = \frac{T_{s,i}\beta_i - T_{s,j}\beta_j - (\beta_i T_i - \beta_j T_j)}{T_{s,j} - T_{s,i}} \quad \text{Equation 7}$$

where $\beta_{obj}$ represents thermal effusivity of the material, $T_{s,i}$ represents a thermal equilibrium temperature of an $i^{th}$ heat generator, $T_{s,j}$ represents a thermal equilibrium temperature of a $j^{th}$ heat generator, $T_i$ represents an initial temperature of the $i^{th}$ heat generator, $T_j$ represents an initial temperature of the $j^{th}$ heat generator, $\beta_i$ represents thermal effusivity of the $i^{th}$ heat generator, and $\beta_j$ represents thermal effusivity of the $j^{th}$ heat generator.

Advantageous Effects

Since the material screening apparatus according to the present disclosure uses a plurality of measured temperature values when calculating a thermal feature value of a material, the reliability for material identification may be enhanced.

In addition, since the material screening apparatus according to the present disclosure senses a temperature change by simply contacting a material to be identified, a thermal feature value of the material may be checked in a simple and easy way.

MODE FOR THE INVENTION

Hereinafter, a material screening apparatus according to an embodiment of the present disclosure will be described in detail with reference to the accompanying drawings.

Figure 1:
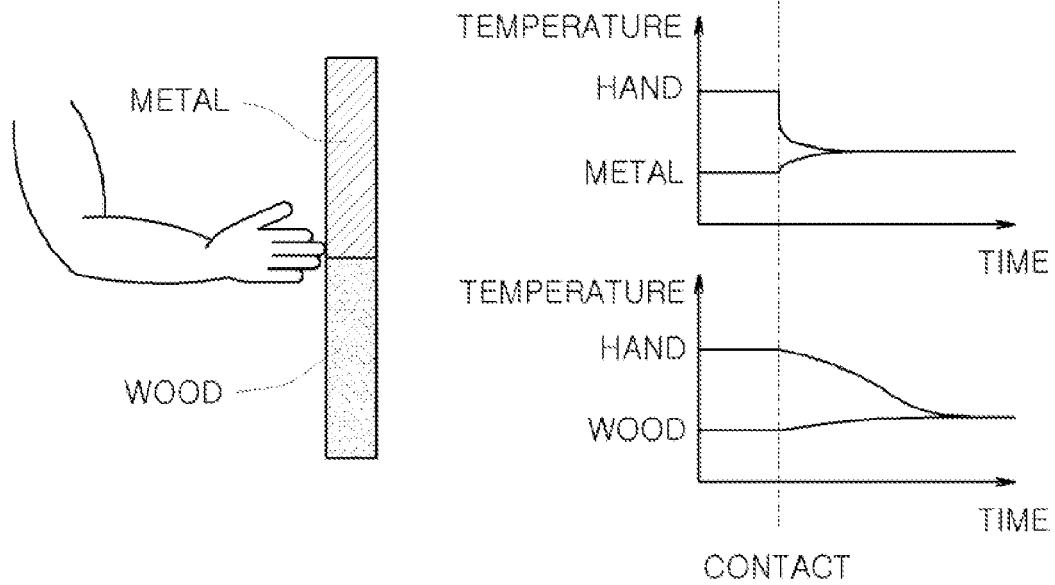
FIG. 1 is a diagram for illustrating an operating principle of a material screening apparatus according to the present disclosure.

FIG. 1 is a diagram for illustrating an operating principle of a material screening apparatus according to the present disclosure.

Referring to FIG. 1, when two materials of different temperatures contact each other, a specific temperature change occurs according to the thermal conductivity characteristics of the materials.

When a person contacts metal and wood of the same temperature, for example of a normal temperature, since metal and wood have different thermal characteristics, the person feels different on the hand even though the metal and the wood initially have the same temperature. This is because different heat flows are generated due to different thermal conductivities of metal and wood as shown in the time-temperature graph of FIG. 1.

In other words, since metal has high thermal conductivity, heat is conducted fast to the hand so that the person feels cold. Meanwhile, since wood has low thermal conductivity, heat is conducted slowly to the hand, and thus the person feels relatively warmer in comparison to the case of metal.

A material screening apparatus according to the present disclosure may calculate a thermal feature value of a material by using the above principle, obtained by the contact of two materials, thereby identifying the kind of a material.

Figure 2:
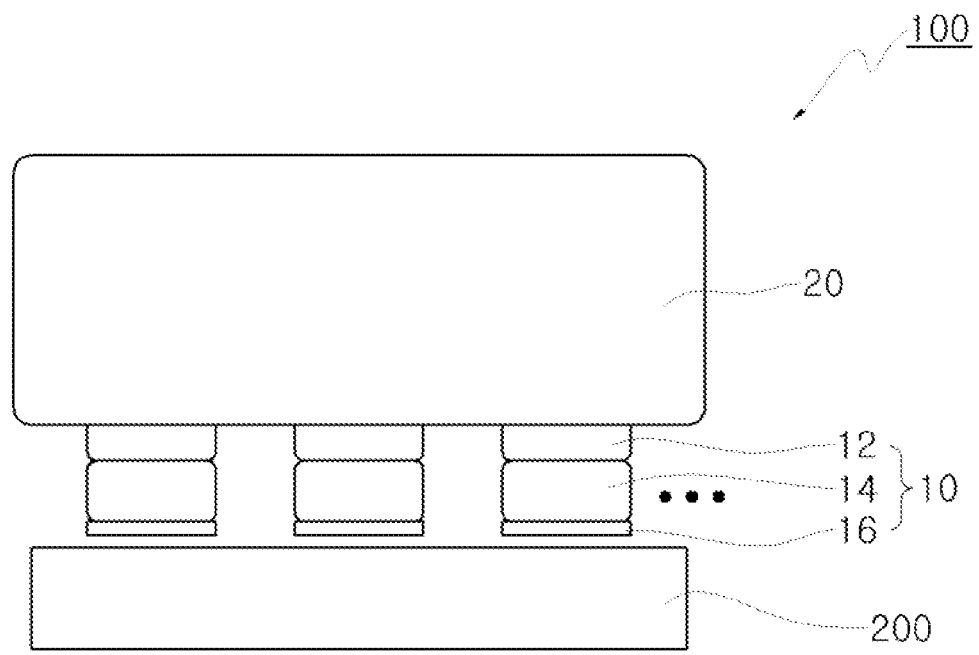
FIG. 2 is a schematic view showing a material screening apparatus according to an embodiment of the present disclosure.

FIG. 2 is a schematic view showing a material screening apparatus according to an embodiment of the present disclosure.

Referring to FIG. 2, the material screening apparatus 100 according to the present disclosure includes a measuring unit 10 and a controller 20.

The measuring unit 10 includes a heat generator 14 and a temperature sensor 16, and selectively further includes a pressure sensor 12.

The measuring unit 10 is connected to the controller 20 and operated according to the control of the controller 20. Even though FIG. 2 depicts three measuring units 10, the number of the measuring units 10 is not limited thereto, and two or more measuring units may be used according to the purpose and measurement reliability.

The heat generators 14 individually generate heat. The plurality of heat generators 14 are arranged at regular intervals, and since the controller 20 plays a role of a heat sink, the heat generators 14 do not interfere in each other. The heat generator 14 may be composed of, for example, a Peltier device, a heat pump or the like, and may also be configured to generate heat according to a control signal of the controller 20.

The temperature sensor 16 is attached to each heat generator 14 and measures a varying temperature of the heat generator 14. In detail, the temperature sensor 16 measures a temperature before the heat generator 14 contacts the material 200, and also measures a temperature when the heat generator 14 contacts the material 200 and comes to an equilibrium temperature. The temperature sensor 16 may be composed of, for example, a thermocouple, a thermistor or the like.

If the heat generator 14 contacts the material 200 to be identified, the pressure sensor 12 senses a pressure change caused by the contact and interrupts heat generation of the heat generator 14. Therefore, if pressure sensors 12 are added, the temperature sensor 16 may measure a temperature change of the heat generator 14 more exactly. The pressure sensor 12 may employ, for example, a load cell, a force sensor or the like.

The controller 20 controls heat generation of the heat generator 14, receives and processes temperature values measured by the temperature sensors 16, and calculates a thermal feature value of the material. In addition, the controller 20 is a movable frame attached to the measuring unit 10 and plays a role of a heat sink for the heat generated by the heat generator 14.

The controller 20 calculates thermal effusivity, which is a thermal feature value of the material, from the temperature values measured by the temperature sensors 16, according to the least square method by applying Equation 1 below.

$$T_{s,i} = \frac{\beta_i T_i + \beta_{obj} T_{obj}}{\beta_i + \beta_{obj}} \quad \text{Equation 1}$$

where $T_{obj}$ represents an initial temperature of the material 200, $T_{s,i}$ represents a thermal equilibrium temperature of an $i^{th}$ heat generator 14, $T_i$ represents an initial temperature of the $i^{th}$ heat generator 14, $\beta_{obj}$ represents thermal effusivity of the material 200, and $\beta_i$ represents thermal effusivity of the $i^{th}$ heat generator 14.

In addition, the thermal effusivity β may be defined according to Equation 2 below.

$$\beta_{(\cdot)} = \sqrt{k_{(\cdot)} c_{(\cdot)} \rho_{(\cdot)}} \quad \text{Equation 2}$$

where k represents thermal conductivity, c represents a specific heat, and ρ represents density. Since every material has inherent k, c, ρ, the thermal effusivity calculated by their combinations also represents an inherent thermal characteristic of the material 200.

In Equation 1, the thermal effusivity $\beta_i$ of the heat generator 14 corresponds to a given value since it is determined according to the material of the $i^{th}$ heat generator 14.

In addition, in Equation 1, since $T_{s,i}$ represents a thermal equilibrium temperature of the $i^{th}$ heat generator 14 and $T_i$ is an initial temperature of the $i^{th}$ heat generator 14, they may be obtained if the temperature sensor 16 measures temperature of the heat generator 14. Therefore, Equation 1 has two unknown values $T_{obj}$ and $\beta_{obj}$.

Meanwhile, in FIG. 2, since an equation such as Equation 1 may be derived through each measuring unit 10, if the number of the measuring units 10 is n, n number of equations is obtained. Here, in the case the least square method is applied thereto, if n is 2 or more, two unknown values $T_{obj}$ and $\beta_{obj}$ may be calculated. As described above, since $\beta_{obj}$ is thermal effusivity of the material to be identified and each material has inherent thermal effusivity, if the $\beta_{obj}$ is known, the kind of the material may be identified.

In detail, if Equation 1 is applied to the $j^{th}$ measuring unit 10, Equation 3 below is obtained.

$$T_{s,j} = \frac{\beta_j T_j + \beta_{obj} T_{obj}}{\beta_j + \beta_{obj}} \quad \text{Equation 3}$$

where $T_{obj}$ represents an initial temperature of the material 200, $T_{s,j}$ represents a thermal equilibrium temperature of a $j^{th}$ heat generator 14, $T_j$ represents an initial temperature of the $j^{th}$ heat generator 14, $\beta_{obj}$ represents thermal effusivity of the material 200, and $\beta_i$ represents thermal effusivity of the $j^{th}$ heat generator 14.

If Equations 1 and 3 are arranged with respect to $T_{obj}$, Equations 4 and 5 below are obtained.

$$T_{obj} = \frac{T_{s,i}(\beta_i + \beta_{obj}) - \beta_i T_i}{\beta_{obj}} \quad \text{Equation 4}$$

-continued $$T_{obj} = \frac{T_{s,j}(\beta_j + \beta_{obj}) - \beta_j T_j}{\beta_{obj}} \quad \text{Equation 5}$$

If Equation 4 is divided by Equation 5, Equation 6 below is obtained.

$$1 = \frac{T_{s,i}(\beta_i + \beta_{obj}) - \beta_i T_i}{T_{s,j}(\beta_j + \beta_{obj}) - \beta_j T_j} \quad \text{Equation 6}$$

If Equation 6 is arranged with respect to $\beta_{obj}$, Equation 7 below is obtained.

$$\beta_{obj} = \frac{T_{s,i}\beta_i - T_{s,j}\beta_j - (\beta_i T_i - \beta_j T_j)}{T_{s,j} - T_{s,i}} \quad \text{Equation 7}$$

where $i \neq j (\cdot) i \neq (\cdot) j$.

Since Equation 7 has no unknown value, $\beta_{obj}$ may be obtained instantly, and if the obtained $\beta_{obj}$ is input to Equation 4 or 5, $T_{obj}$ is also calculated.

In addition, in order to calculate an identification result of the material, the controller 20 may include a storage unit (not shown), a comparing unit (not shown) and/or a display unit (not shown).

The storage unit stores inherent thermal feature values of a plurality of materials in a table format in advance.

The comparing unit compares the thermal feature value of the material, calculated from the temperature values measured by the plurality of temperature sensors 16, with data values stored in the storage unit to find a coincident value.

The display unit displays the identification result of the material 200 checked by the comparing unit. If a coincident value is present according to a comparison result of the comparing unit, the display unit may display the corresponding information of the material 200. Meanwhile, if a coincident value is not present according to a comparison result of the comparing unit, the display unit may display a message notifying that it is impossible to identify the kind of the material 200.

The material screening apparatus 100 according to the present disclosure may be utilized as a subminiature material identifying apparatus having a measuring unit array composed of a plurality of measuring units 10, by applying the MEMS technique.

The embodiment has been disclosed just for exemplary illustration, and it will be understood by those skilled in the art that various changes, modifications and additions can be made thereto without departing from the spirit and scope of the present disclosure, and such changes, modifications and additions should be regarded as belonging to the appended claims.

The invention claimed is:

1. A material screening apparatus, which identifies a material by contacting a surface of the material and calculating a thermal feature value of the material, the apparatus comprising:
   heat generators configured to individually generate heat;
   temperature sensors respectively attached to the heat generators and configured to measure temperatures of the heat generators; and
   a controller configured to control heat generation of the heat generators, process temperature values measured by the temperature sensors, and calculate a thermal feature value of the material,
   wherein the controller calculates thermal effusivity, which is the thermal feature value of the material, by applying the temperature values measured by the temperature sensors to the equation:

$$\beta_{obj} = \frac{T_{s,i}\beta_i - T_{s,j}\beta_j - (\beta_i T_i - \beta_j T_j)}{T_{s,j} - T_{s,i}}$$

where $\beta obj$ represents thermal effusivity of the material,
$T_{s,i}$ represents a thermal equilibrium temperature of an $i^{th}$ heat generator,
$T_{s,j}$ represents a thermal equilibrium temperature of a $j^{th}$ heat generator,
$T_i$ represents an initial temperature of the $i^{th}$ heat generator,
$T_j$ represents an initial temperature of the $j^{th}$ heat generator,
$\beta_i$ represents thermal effusivity of the $i^{th}$ heat generator, and
$\beta_j$ represents thermal effusivity of the $j^{th}$ heat generator.

2. The material screening apparatus according to claim 1, further comprising a pressure sensor configured to, when the heat generator contacts the material to be identified, sense a pressure change caused by the contact and intercept heat generation of the heat generators.

3. The material screening apparatus according to claim 1, wherein the controller comprises:
   a storage unit configured to store inherent thermal feature values of materials; and
   a comparing unit configured to compare the thermal feature value of the material being identified, calculated from the temperature values measured by the temperature sensors, with data values stored in the storage unit to find a coincident value.

4. The material screening apparatus according to claim 3, wherein the controller further comprises a display unit configured to display an identification result of the material, compared by the comparing unit.

* * * * *